United States Patent [19]

Jarque et al.

[11] 4,174,451
[45] Nov. 13, 1979

[54] 2-FURYL-(3,4-DIMETHYL-2-PYRIDYL)-CARBINOL

[75] Inventors: Ricardo Granados Jarque; Juan Bosch Cartes; Rosa Llobera Jimenez, all of Barcelona; Cristobal Martinez Roldán; Fernando Rabadan Peinado, both of Madrid, all of Spain

[73] Assignee: Laboratorios Made, S.A., Madrid, Spain

[21] Appl. No.: 949,022

[22] Filed: Oct. 6, 1978

[30] Foreign Application Priority Data

Oct. 7, 1977 [ES] Spain ............................. 462.987

[51] Int. Cl.$^2$ ........................................... C07D 405/02
[52] U.S. Cl. ..................................... 546/283; 424/263
[58] Field of Search ........................................ 546/283

[56] References Cited

PUBLICATIONS

Tilford et al., J. Am. Chem. Soc. vol. 70, pp. 4001–4009 (1948).
Sperber et al., J. Am. Chem. Soc. vol. 71, pp. 887–890 (1948).
McCarty et al., J. Am. Chem. Soc. vol. 79, pp. 472–480 (1957).
Zelinski et al., J. Am. Chem. Soc. vol. 73, pp. 696–697 (1951).
Klein, Ber. Deut. Chem. vol. 23, pp. 2693–2696 (1890).
Abramovitch, Pyridine and Its Derivatives, vol. 14 Supplement Part 2, pp. 498–499 and 506–508, John Wiley and Sons, NY (1974).
Klingsberg, Pyridine and Its Derivatives, Part 4, pp. 27, 31, 33–41, Interscience Publishers, NY (1964).

Primary Examiner—John D. Randolph
Attorney, Agent, or Firm—Haseltine, Lake & Waters

[57] ABSTRACT

Furfural is reacted with 2-bromo-3,4-dimethylpyridine in an ether solution of butyl-lithium at about −15° C. in an inert atmosphere to form 2-furyl-(3,4-dimethyl-2-pyridyl)-carbinol, having analgesic properties.

6 Claims, No Drawings

2-FURYL-(3,4-DIMETHYL-2-PYRIDYL)-CARBINOL

The present invention relates to the preparation of 2-furyl-(3,4-dimethyl-2-pyridyl)-carbinol of formula I.

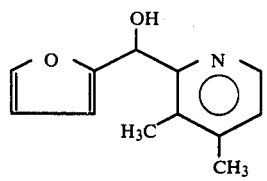

The above compound is a novel substance of possible interest as an analgesic, and is prepared, according to the method of the invention, by reacting furfural in an inert atmosphere with 2-bromo-3,4-dimethylpyridine in an ether solution of butyl-lithium. The reaction is carried out between the temperatures of −40° C. maintained during the addition of butyl-lithium to the 2-bromo-3,4-dimethylpyridine, −25° C. maintained during the addition of furfural in anhydrous ether and −15° C. during the course of the reaction.

The resulting mixture is poured over an aqueous solution of ammonium chloride and is extracted with ether. After evaporation of the solvent the resulting oil is purified by chromatography in a silica gel column, obtaining the 2-furyl-(3,4-dimethyl-2-pyridyl)-carbinol (I).

The following example is given only as an illustration and is in no way to be considered as limiting the scope of the invention.

EXAMPLE Preparation of 2-furyl-(3,4-dimethyl-2-pyridyl)-carbinol (I)

To 120 ml of a 0.74 M ether solution of butyl-lithium, there is slowly added under nitrogen atmosphere a solution of 10 g of 2-bromo-3,4-dimethylpyridine in 25 ml of anhydrous ether, the temperature being maintained at −40° C. Once the addition is concluded stirring is continued for one hour and 30 minutes, maintaining the same temperature. The temperature is increased to −25° C. and a solution of 5.3 ml of recently distilled furfural in 10 ml of anhydrous ether is added dropwise, following which the temperature is increased to −15° C. and the mixture is stirred for one hour. The reaction mixture is poured over 10% hydrochloric acid to acid pH, cooling from the exterior with ice. The aqueous layer is made alkaline with 10% sodium hydroxide, is cooled from the exterior and is extracted with ether. The ether layer is dried over anhydrous sodium sulphate, filtered and evaporated to dryness, the result being 4.9 g of an oil which is purified by filtration through a silica gel column. The fractions eluated with 95/5 and 70/30 proportions of benzene/chloroform, are collected to obtain 2.65 g (Yield 24%) of 2-furyl-(3,4-dimethyl-2-pyridyl)-carbinol (I). An analytical sample recrystallized from ethyl alcohol has a melting point of 61°–62° C. Calculated analysis for $C_{12}H_{13}NO_2$: C.70.91; H.6.45; N.6.89. Found: C.70.65; H.6.45; N. 6.88.

PHARMACOLOGICAL PROPERTIES OF THE PRODUCT OF THE INVENTION

This product has analgesic activity. Its toxicity and activity have been compared with those of dextropropoxyphene.

A. ACUTE TOXICITY

An acute toxicity study was made on Swiss I.C.R. albino mice of both sexes of 30±2 g in weight, kept without food for 24 hours prior to the experiment. Ambient temperature and relative humidity were kept constant. The products were administered intraperitoneally, the number of deaths being counted 48 hours after treatment. The lethal dose ($LD_{50}$) was calculated by the Litchfield-Wilcoxon test. The results obtained were:

TABLE I

| Product | $LD_{50}$ (mg/kg) |
|---|---|
| I | 309.2 |
| Dextropropoxyphene | 140 |

B. ANALGESIC ACTIVITY

1. Thermal analgesia

The thermal analgesic effect was studied in Swiss I.C.R. albino mice. The 55° C. Hot Plate technique was used. Batches of 10 mice were used.

The products under study were administered intraperitoneally, and after 30 minutes the mice were placed on the hot plate, count being made of the time, in seconds, it took them to jump. Batches of control animals were injected only with distilled water.

The results are shown in Table II.

TABLE II

| Treatment | Dose mg/kg | Jumping time in sec. $\bar{x}$ + S.E.M.[1] | Signif. of differences Control | Dextroprop. |
|---|---|---|---|---|
| Control | — | 63.7 ± 4.54 | — | — |
| I | 30 | 110.1 ± 13.28 | p<0.005 | N.S. |
| Dextroprop. | 30 | 116.8 ± 12.43 | p<0.01 | — |

[1]Mean values ± standard error of the mean.

Product I has the same thermal analgesic action as the dextropropoxyphene.

2. Chemical analgesia

The analgesic effect was studied in Swiss I.C.R. albino mice, by the acetic acid writhing technique. Batches of 10 mice were made.

The products under study were administered intraperitoneally, and 30 minutes later 0.25 ml of 1% acetic acid was injected intraperitoneally. A batch of control animals received only the acetic acid. Twenty minutes following administration of the acetic acid, the number of writhes in each mouse was counted.

The results are shown in Table III.

TABLE III

| Treatments | Dose mg/kg | No. of writhes $\bar{x}$ ± S.E.M.[1] | Signif. of differences Control | Dextroprop. |
|---|---|---|---|---|
| Control | — | 78.4 ± 6.7 | — | — |
| I | 30 | 53 ± 6.07 | p<0.02 | p<0.00005 |
| Dextroprop. | 30 | 8.4 ± 4.04 | p<0.00005 | — |

Product I has chemical analgesic action, but of lesser intensity than that of dextropropoxyphene.

The following are claimed as the novel points of invention filed as the object of this patent application:

1. 2-Furyl-(3,4-dimethyl-2-pyridyl)-carbinol.

2. A process for obtaining 2-furyl-(3,4-dimethyl-2-pyridyl)-carbinol comprising the steps of reacting furfural with 2-bromo-3,4-dimethylpyridine in butyl-lithium at about −15° C. and isolating the product.

3. The process of claim 2 wherein the butyl-lithium is added to the 3,4-dimethylpyridine at about −40° C. and furfural is then added to the resultant mixture at about −25° C.

4. The process of claim 2 or 3 wherein the reaction is carried out in ethyl ether solution under an inert atmosphere.

5. The process of claim 4 wherein the product is isolated by acidifying the reaction mixture with hydrochloric acid, making the aqueous layer alkaline with sodium hydroxide, extracting the alkaline layer with ethyl ether, evaporating the ether, purifying the resultant oil by chromatography through a silica gel column.

6. The process of claim 4 wherein the product is isolated by pouring the reaction mixture into an aqueous solution of ammonium chloride, extracting with ether, evaporating the ether, and purifying the resultant oil by chromatography.

* * * * *